United States Patent [19]

Rebafka et al.

[11] Patent Number: 4,613,683

[45] Date of Patent: Sep. 23, 1986

[54] PREPARATION OF ALKYL GALLATES

[75] Inventors: Walter Rebafka, Hirschberg; Helmüt Nickels, Mutterstadt, both of Fed. Rep. of Germany

[73] Assignee: BASF Aktiengesellschaft, Ludwigshafen, Fed. Rep. of Germany

[21] Appl. No.: 694,937

[22] Filed: Jan. 25, 1985

[30] Foreign Application Priority Data

Feb. 2, 1984 [DE] Fed. Rep. of Germany ....... 3403575

[51] Int. Cl.$^4$ ............................................ C07C 69/88
[52] U.S. Cl. ..................................................... 560/67
[58] Field of Search .......................................... 560/67

[56] References Cited

U.S. PATENT DOCUMENTS 3,511,874  5/1970  Allan ..................................... 560/67

OTHER PUBLICATIONS

Morris et al, J. Am. Oil Chem. Soc., 1947, pp. 309–311.
J. Appl. Chem. Biotechnol., 22, 1972, pp. 559–564.

*Primary Examiner*—Paul J. Killos
*Attorney, Agent, or Firm*—John H. Shurtleff

[57] ABSTRACT

$C_1$–$C_{20}$-alkyl gallates are prepared by reacting tannin-containing material with the corresponding alcohol R—OH and a strong acid.

11 Claims, No Drawings

PREPARATION OF ALKYL GALLATES

The present invention relates to an improved process for the preparation of alkyl gallates of the general formula I

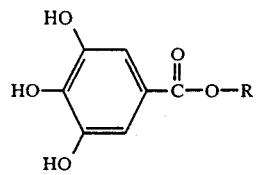

where R is $C_1$-$C_{20}$-alkyl.

Gallic acid is known to be a very effective, and also physiologically acceptable, antioxidant for food, feeds and cosmetic preparations, but has the disadvantage of being poorly soluble in fats, i.e. precisely in the substances which it is primarily desired to stabilize.

Hence, it has also long been known (Morris et al, *J. Am. Oil Chem. Soc.*, 1947, pages 309–311) that, instead of the free gallic acid, its substantially more lipophilic alkyl esters can be used for stabilizing fats and fat-containing formulations.

Accordingly, various processes for the preparation of these esters have been developed, these being described in the synopsis by Wijesekera et al. (*J. Appl. Chem. Bio-technol.*, 22, 1972, pages 559–564). In all of these processes, the starting material used is pure gallic acid, which in turn is obtained by hydrolysis of tannin-containing material followed by a very expensive isolation procedure; hence, the overall preparation of the esters is so expensive that, in spite of their good antioxidative properties, they have not been used to any significant extent to date.

It is an object of the present invention to make the gallates I available by a more economical route, starting from tannin-containing material.

We have found that this object is achieved by a process for the preparation of alkyl gallates of the general formula I

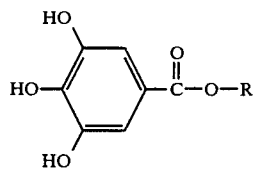

where R is $C_1$-$C_{20}$-alkyl, wherein tannin-containing material is reacted with an alcohol R-OH (II) and a strong acid.

Particularly suitable tannin-containing materials are those from the group consisting of the hydrolyzable tanning agents, which contain water-soluble esters of gallic acid and digallic acid with sugars. They are obtained by extracting parts of plants, e.g. of tara, myrobalan, valonea, sumach, div-divi and aleppo gall, with water. These hydrolyzable tanning agents are commercially available and are generally in the form of a dry powder; they are preferably used in this form in the novel process, since they are readily or very readily soluble in the alcohols II.

The novel process is most advantageously carried out in the absence of water, and it is therefore preferable if the water formed and that present in the reactants are removed continuously by distillation.

Examples of suitable strong acids are sulfuric acid, hydrochloric acid and p-toluenesulfonic acid, in anhydrous form. Even catalytic amounts of the acid are sufficient but in this case very long reaction times have to be accepted. As a rule, higher concentrations are therefore preferable, e.g. from 10 to 50% by weight, based on the amount of the tannin employed.

Among the alcohols II conforming to the definition, the straight-chain alkanols are preferred. The process is particularly important for the preparation of the n-propyl, n-octyl and n-dodecyl esters I, since these substances are already established antioxidants for food and feeds.

To achieve very substantial conversion of the tannin, the alcohol is advantageously used in stoichiometric amounts with respect to the content of the gallic acids in tannin. As a rule, however, it is preferable to use the alcohol in as much as about a 30-fold molar excess over the bound gallic acid.

With regard to the process, it is advantageous if the tannin is dissolved in the alcohol, the acid is added or, if it is gaseous as in the case of HCl, is passed in, and the mixture is heated at the boil with removal of the water by distillation. However, because of the thermal sensitivity of the gallic acid, temperatures higher than 150° C. should be avoided, especially for prolonged periods. If it is water-insoluble or only sparingly soluble in water, the alcohol which passes over in the vapor phase can be condensed and then recycled to the reaction.

The reaction mixture can be worked up in a conventional manner by neutralizing the acid with aqueous alkali, separating off the phase consisting of water-insoluble alcohol II and ester I, washing this phase with water, drying it and, if necessary, evaporating it down, and crystallizing the ester I. If the alcohol is a water-soluble one, it is first distilled off, the ester phase separating out; the ester is then taken up in a water-insoluble organic solvent, e.g. in diethyl ether, toluene, chlorobenzene, methylene chloride or a higher alcohol, and is precipitated or recrystallized from this solution.

The esters I which are obtained directly in this manner generally have a purity of 60–80%. They still contain the original natural product components as by-products and can therefore be used in this form as antioxidants for feeds.

Fairly high and very high purities are achieved by recrystallization, for example from chlorobenzene, alcohols or toluene or, in the case of the lower esters, from water or methanol/water mixtures.

Because the gallates are sensitive to oxidation, it is preferable to carry out all operations substantially in the absence of atmospheric oxygen, i.e. under an inert gas atmosphere.

EXAMPLE 1

Preparation of N-propyl gallate

A mixture of 500 g of tara (theoretical gallic acid content about 1.5 moles), 2,000 g (33.3 moles) of n-propanol and 50 g of anhydrous sulfuric acid was refluxed at 100° C. for 25 hours, the water of reaction being removed continuously in the form of a propanol/water azeotrope.

When water was no longer eliminated, the mixture was neutralized with dilute sodium hydroxide solution and freed from excess propanol by distillation.

The residue was taken up in a mixture of 900 ml of isobutanol and 600 ml of n-butanol, and this solution was then washed with a total of 6 l of water.

The organic phase was evaporated down, after which 400 g of a crude n-propyl gallate having a purity of 60% (according to HPLC analysis) were obtained in the form of an oil. The yield was 75%, based on the gallic acid content of the tara used, and converted to pure ester.

Recrystallization from water gave the ester in a yield of 60% and with a purity of 95%.

EXAMPLE 2

Preparation of N-octyl gallate

A mixture of 30 g of tara (about 0.1 mole of bound gallic acid), 120 g (0.95 mole) of n-octanol and 3 g of anhydrous sulfuric acid was heated at 140° C. for 7 hours with continuous removal of the water of reaction, after which the mixture was washed neutral with water and then evaporated down to give the crude n-octyl gallate in the form of an oil. The purity of the product was 65% and the yield was 75%, calculated as pure ester.

Recrystallization from dichloropropane gave the ester in a yield of 65% and with a purity of 95%.

We claim:

1. A process for the preparation of an alkyl gallate of the formula

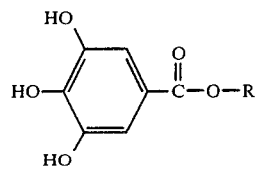

where R is $C_1$–$C_{20}$-alkyl, which process comprises:
  reacting a tannin with an alcohol R-OH, wherein R has the above meaning, and a strong acid in catalytic amounts up to 50% by weight, based on the amount of the tannin employed.

2. A process as claim 1 wherein the tannin is selected from the group consisting of the hydrolyzable tanning agents which contain water-soluble esters of gallic acid and digallic acid with sugars.

3. A process as claimed in claim 1 wherein water formed during the reaction is continuously removed by distillation.

4. A process as claimed in claim 1 wherein the alcohol is used in an excess of up to about a 30-fold molar excess with reference to the bound gallic acid.

5. A process as claimed in claim 1 wherein the reaction is carried out under an inert gas atmosphere.

6. A process as claimed in claim 1 wherein the reaction is carried out at the boil with a temperature no higher than about 150° C.

7. A process as claimed in claim 1 wherein the strong acid is sulfuric acid.

8. a process as claimed in claim 1 wherein the reaction is carried out in a solution of the tannin dissolved in excess alcohol, at the boiling point of the reaction mixture but not higher than about 150° C., under an inert atmosphere and in the presence of about 10 to 50% by weight of the strong acid.

9. A process as claimed in claim 8 wherein the strong acid is sulfuric acid.

10. A process as claimed in claim 8 wherein the alcohol is used in an excess of up to about a 30-fold molar excess with reference to the bound gallic acid.

11. A process as claimed in claim 10 wherein the strong acid is sulfuric acid.

* * * * *